United States Patent
Harada et al.

(10) Patent No.: US 10,436,806 B2
(45) Date of Patent: Oct. 8, 2019

(54) METHOD OF MEASURING LIPOPROTEIN'S CAPACITY TO ACCEPT CHOLESTEROL

(71) Applicant: SYSMEX CORPORATION, Kobe-shi, Hyogo (JP)

(72) Inventors: Amane Harada, Kobe (JP); Katsuhiro Murakami, Kobe (JP); Maria Kiriyama, Kobe (JP); Keiko Yoshikawa, Akashi (JP); Keiko Miwa, Suita (JP)

(73) Assignee: SYSMEX CORPORATION, Kobe-shi, Hyogo (JP)

( * ) Notice: Subject to any disclaimer, the term of this patent is extended or adjusted under 35 U.S.C. 154(b) by 927 days.

(21) Appl. No.: 14/882,812

(22) Filed: Oct. 14, 2015

(65) Prior Publication Data
US 2016/0109469 A1    Apr. 21, 2016

(30) Foreign Application Priority Data

Oct. 16, 2014  (JP) ................ 2014-211703
Aug. 19, 2015  (JP) ................ 2015-161937

(51) Int. Cl.
*G01N 33/53* (2006.01)
*G01N 33/92* (2006.01)

(52) U.S. Cl.
CPC ....... *G01N 33/92* (2013.01); *G01N 2333/775* (2013.01); *G01N 2405/00* (2013.01); *G01N 2800/044* (2013.01)

(58) Field of Classification Search
None
See application file for complete search history.

(56) References Cited

FOREIGN PATENT DOCUMENTS

| EP | 1 114 870 A1 | 7/2001 |
|---|---|---|
| WO | 93/18067 A1 | 9/1993 |
| WO | 2012/104411 A1 | 8/2012 |

OTHER PUBLICATIONS

Vogel et al., A Rapid Method for Separation of Plasma Low and High Density Lipoproteins for Tocopherol and Carotenoid Analyses, Lipids, vol. 31, No. 4, 1996, pp. 421-426. (Year: 1996).*
Marks et al., Use of Bodipy-labeled sphingolipid and cholesterol analogs to examine membrane microdomains in cells, Histochem Cell Biod, 2008, 130, pp. 819-832. (Year: 2008).*
Gaibelet et al., "21-Methylpyrenyl-cholesterol stably and specifically associates with lipoprotein peripheral hemi-membrane: A new labelling tool", Biochemical and Biophysical Research Communications, Oct. 5, 2013, vol. 440, No. 4, pp. 533-538.
Heuck et al., "Cholesterol Determination in Serum after Fractionation of Lipoproteins by Immunoprecipitation", Clin. Chem., Feb. 1, 1985, vol. 31, No. 2, pp. 252-256.
Meyer et al., "Cholesterol analogues for research—nothing is like the original!", Biospektrum, Mar. 1, 2012, vol. 18, No. 2, pp. 142-145 (13 pgs. total).
Amit V. Khera, M.D., et al., "Cholesterol Efflux Capacity, High-Density Lipoprotein Function, and Atherosclerosis", The New England Journal of Medicine, Jan. 13, 2011, pp. 127-135, vol. 364, No. 2.
Sandhya Sankaranarayanan, et al., "A sensitive assay for ABCA1-mediated cholesterol efflux using BODIPY-cholesterol", Journal of Lipid Research, 2011, pp. 2332-2340, vol. 52.

* cited by examiner

*Primary Examiner* — Gary Counts
(74) *Attorney, Agent, or Firm* — Sughrue Mion, PLLC

(57) ABSTRACT

Provided is a method of measuring a lipoprotein's capacity to accept cholesterol including the steps of bringing a lipoprotein in a sample into contact with labeled cholesterol to incorporate the labeled cholesterol into the lipoprotein, bringing the lipoprotein having the labeled cholesterol into contact with an antibody that binds to a lipoprotein to form a complex of the lipoprotein and the antibody, and measuring the label incorporated into the complex.

18 Claims, 4 Drawing Sheets

METHOD OF MEASURING LIPOPROTEIN'S CAPACITY TO ACCEPT CHOLESTEROL

CROSS REFERENCE TO RELATED APPLICATIONS

This application claims priority from prior Japanese Patent Application No. 2014-211703, filed on Oct. 16, 2014, entitled "METHOD OF MEASURING HIGH DENSITY LIPOPROTEIN'S CAPACITY TO ACCEPT CHOLESTEROL AND REAGENT KIT", the entire contents of which are incorporated herein by reference.

This application claims priority from prior Japanese Patent Application No. 2015-161937, filed on Aug. 19, 2015, entitled "METHOD OF MEASURING HIGH DENSITY LIPOPROTEIN'S CAPACITY TO ACCEPT CHOLESTEROL AND REAGENT KIT", the entire contents of which are incorporated herein by reference.

TECHNICAL FIELD

The present disclosure relates to a method of measuring lipoprotein's capacity to accept cholesterol.

BACKGROUND

Disorders of lipid metabolism are associated with various types of diseases including diabetes and cardiovascular diseases (CVD). Blood concentrations of lipids, such as triglycerides and cholesterol, are known to provide indications of the abnormal lipid metabolism. However, the concentration of cholesterol carried by lipoproteins, such as high-density lipoprotein (HDL), does not always reflect the presence and risk of these diseases. Not only quantitative indices (such as the concentration of cholesterol) but also qualitative indices focused on the functionality of lipoproteins have attracted attention.

For example, several reports have shown that some HDL cholesterol (HDL-C) raising agents, such as CETP inhibitors, did not reduce the risk of CVD even though they effectively increased the blood concentration of HDL-C. This indicates the possibility that the concentration of HDL-C does not completely reflect the risk of CVD. Recently, attention has focused on the physiological functions of high-density lipoprotein (HDL) to monitor the risk of CVD. It has been reported that the HDL's capacity to excrete cholesterol from the peripheral tissue is a negative prognostic factor for the risk of CVD.

As the method of examining the functionality of HDL, a method of using fluorescence-labeled cholesterol and cultured cells is described in, for example, Sankaranarayanan S. et. al, A sensitive assay for ABCA1-mediated cholesterol efflux using BODIPY-cholesterol. J. Lipid Res., vol. 52, p. 2332-2340 (2001). In this method, functional level of HDL to promote cholesterol excretion from cells is examined by measuring the removal amount of fluorescence-labeled cholesterol from the macrophages containing the labeled cholesterol by HDL. This method includes the following four steps: (1) incorporating labeled cholesterol into macrophage cells; (2) adding an inhibitor for acyl-CoA: cholesterol acyltransferase to inhibit the esterification of cholesterol in the cells; (3) adding HDL to stimulate the macrophages; and (4) recovering the culture supernatant and cell lysate and quantifying the labeled cholesterol in these liquids.

On the other hand, PCT International Publication No. WO 2012/104411 describes a method of determining the presence of dyslipidemia by fluorescence-labeled cholesterol without using cultured cells. In this method, the peripheral monolayers of various lipoproteins including low-density lipoprotein (LDL), HDL or the like is labeled with fluorescence-labeled cholesterol (cholesterol pyrene), and it is determined whether a subject has dyslipidemia based on the fluorescence spectra obtained by measuring the labeled lipoproteins. The literature describes that the labeled lipoproteins can be separated from fluorescence-labeled free cholesterol by ultracentrifugation, dialysis or FPLC using a gel-filtration column.

SUMMARY OF THE INVENTION

The scope of the present invention is defined solely by the appended claims, and is not affected to any degree by the statements within this summary.

There is provided a method of measuring a lipoprotein's capacity to accept cholesterol comprising the steps of: bringing a lipoprotein in a sample into contact with labeled cholesterol to incorporate the labeled cholesterol into the lipoprotein; bringing the lipoprotein having the labeled cholesterol into contact with an antibody that binds to the lipoprotein to form a complex of the lipoprotein and the antibody; and measuring the label generated from the complex.

There is also provided a method of measuring a lipoprotein's capacity to accept cholesterol comprising the steps of: bringing a high-density lipoprotein in a sample into contact with labeled cholesterol to incorporate the labeled cholesterol into the high-density lipoprotein; bringing the high-density lipoprotein having the labeled cholesterol into contact with an antibody that binds to a high-density lipoprotein to form a complex of the high-density lipoprotein and the antibody; and measuring the label generated from the complex. In this method, the step of incorporating the labeled cholesterol into the high-densitylipoprotein, the step of forming the complex, and the step of measuring the label are performed in a cell-free system.

There is also provided a method of measuring a lipoprotein's capacity to accept cholesterol comprising the steps of: bringing a high-density lipoprotein in a sample into contact with labeled cholesterol to incorporate the labeled cholesterol into the high-density lipoprotein; bringing the high-density lipoprotein having the labeled cholesterol into contact with an anti-apolipoprotein AI (ApoAI) antibody which is immobilized on a solid phase to form a complex of the high-density lipoprotein and the anti-ApoAI antibody on the solid phase; and measuring the label generated from the complex. In this method, the step of incorporating the labeled cholesterol into the high-densitylipoprotein, the step of forming the complex, and the step of measuring the label are performed in a cell-free system.

DETAILED DESCRIPTION OF THE PREFERRED EMBODIMENTS

Figure 1:
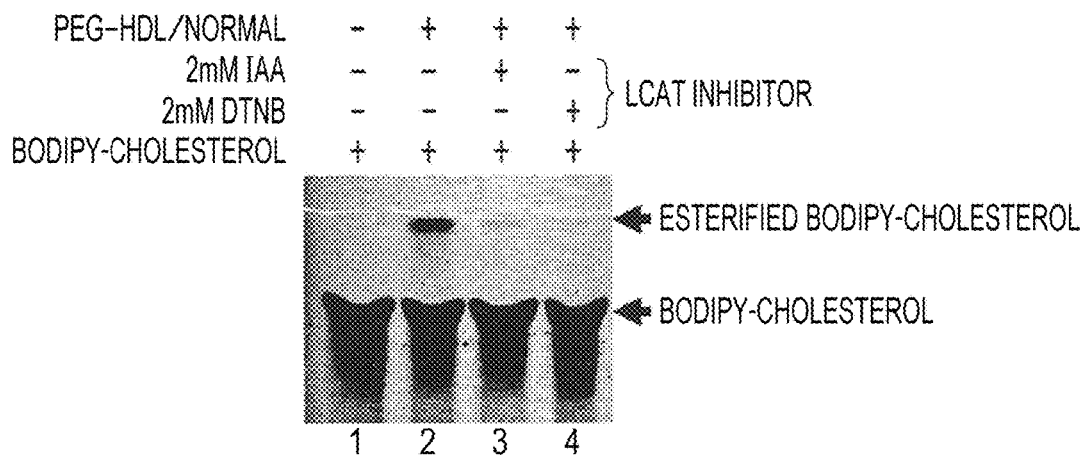
FIG. 1 is a photograph showing that fluorescence-labeled cholesterol including a fluorophore having a boron-dipyrromethene skeleton is esterified by HDL.

In the method of measuring a lipoprotein's capacity to accept cholesterol of the embodiment (hereinafter, simply referred to as "measurement method"), as described below, labeled cholesterol is directly incorporated into a lipoprotein in a sample. In the conventional method (for example, the method described in Sankaranarayanan S. et. al, A sensitive assay for ABCA1-mediated cholesterol efflux using BODIPY-cholesterol. J. Lipid Res., vol. 52, p. 2332-2340 (2001), which is incorporated herein by reference), cells such as macrophages are necessary. However, the present embodiment does not require the use of cholesterol-accumulated cells such as macrophages. In any of the following steps, the measurement method of the embodiment can be performed in a cell-free system. The cell-free system means that no cell is added in order to measure the lipoprotein's capacity to accept cholesterol. Hence, the measurement method of the embodiment can be performed without using the properties and functions of the cell added for the measurement. In the embodiment, even when a sample to be used contains a subject-derived cell, the measurement method assumes that the cell itself has little influence on the uptake of the labeled cholesterol by the lipoprotein and the measurement method is recognized as a cell-free system.

In the measurement method of the embodiment, the step to be performed is the step of bringing a lipoprotein in a sample into contact with labeled cholesterol to incorporate the labeled cholesterol into lipoprotein. In the embodiment, there is no particular limitation as to the sample as long as it includes a mammalian lipoprotein, preferably a human lipoprotein. Examples of samples include blood samples such as whole blood, serum, and plasma.

The lipoprotein to be used as a measuring object of the embodiment may be HDL, LDL, intermediate density lipoprotein (IDL), very low density lipoprotein (VLDL) or chylomicron (CM). HDL is a lipoprotein having a density of 1.063 g/mL or more. LDL is a lipoprotein having a density of 1.019 g/mL or more and less than 1.063 g/mL. IDL is a lipoprotein having a density of 1.006 g/mL or more and less than 1.019 g/mL. VLDL is a lipoprotein having a density of 0.95 g/mL or more and less than 1.006 g/mL. CM is a lipoprotein having a density of less than 0.95 g/mL. In a preferred embodiment, among the lipoproteins, HDL is used as an object to be measured.

In the measurement of the embodiment, a fraction containing a predetermined lipoprotein can be obtained by separating a blood sample by any known method such as ultracentrifugation or polyethylene glycol (PEG) precipitation.

In the embodiment, a solution prepared by diluting the blood sample and the fraction containing a predetermined lipoprotein with an aqueous medium may be used as a sample in order to adjust the lipoprotein concentration.

Examples of aqueous media include water, physiological saline, and buffers such as phosphate buffered saline (PBS) and Tris-HCl. As for the lipoprotein concentration in the sample, the concentration of ApoAI as a main component of the lipoprotein serves as an index. Thus, in the embodiment, the concentration of ApoAI in a part of the sample may be measured by known immunoassay (e.g., immunonephelometry). Based on the concentration of the obtained ApoAI, the lipoprotein concentration in the sample can be adjusted.

If necessary, bovine serum albumin (BSA) or a blocking agent such as liposome may be added to the sample. It is known that the lipoprotein esterifies cholesterol and absorbs it. Accordingly, a fatty acid necessary for the esterification of the cholesterol by the lipoprotein or a composition containing the fatty acid (e.g., liposome) may be added to the sample.

In the method of the embodiment, labeled cholesterol is used to incorporate the cholesterol into a lipoprotein. The labeled cholesterol is a substance in which a labeled molecule binds to a part of a molecule of cholesterol. The cholesterol moiety in the labeled cholesterol may have a structure of naturally occurring cholesterol or a structure of cholesterol in which one or more methylene and/or methyl groups are removed from an alkyl chain bound to the C17 position of naturally occurring cholesterol (also referred to as non-cholesterol).

As described above, the lipoprotein esterifies cholesterol and absorbs it. Thus, it is more preferable to use labeled cholesterol which is esterified by the lipoprotein. In the method of the embodiment, when the labeled cholesterol is brought into contact with a sample, the labeled cholesterol is esterified by lecithin-cholesterol acyltransferase (LCAT) derived from the living body in the sample. The method of confirming the esterification of the labeled cholesterol by the lipoprotein is known in the art. Those skilled in the art are able to routinely perform the method.

The label is preferably a substance which generates a detectable signal from the label itself. Examples of substances include fluorescent substances, coloring substances, and luminescent materials. Among them, the fluorescent substances are particularly preferred. Preferably, the fluorescent substances include a fluorophore having a polar structure. Fluorescent-labeled cholesterol and labeled substances including a fluorophore having a polar structure are known in the art.

The fluorescence-labeled cholesterol including a fluorophore having a polar structure is, for example, fluorescence-labeled cholesterol including a fluorophore having a boron-dipyrromethene (BODIPY®) skeleton represented by the following formula (I):

[Formula 1]

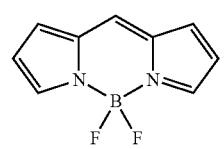

(I)

or a benzoxadiazole skeleton represented by the following formula (II):

[Formula 2]

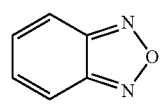

(II)

The labeled cholesterol can be produced by adding a label to cholesterol by any known method. There is no particular limitation as to the position of the label to be added to the cholesterol and it can be appropriately determined according to the label to be used. There is no particular limitation as to the bonding of the label to the cholesterol. It is preferable that both the label and the cholesterol are directly bound via a covalent bond.

In the embodiment, commercially available labeled cholesterol may be used. For example, the fluorescence-labeled cholesterol including a fluorophore having a BODIPY skeleton includes fluorescence-labeled cholesterol represented by the following formula (III):

[Formula 3]

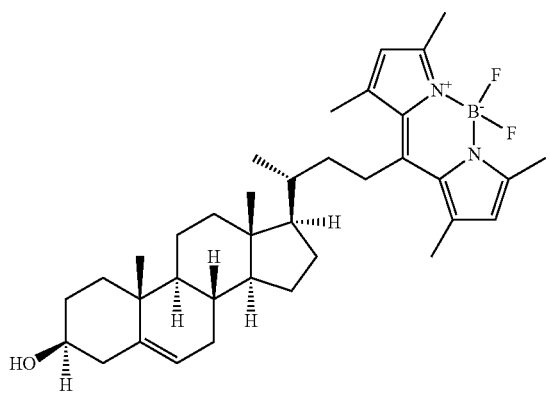

(III)

(23-(dipyrro-metheneboron-difluoride)-24-norcholesterol), product name: TopFluor Cholesterol, CAS No: 878557-19-8, available from Avanti Polar Lipids, Inc.).

The fluorescence-labeled cholesterol including a fluorophore having a benzoxadiazole skeleton includes fluorescence-labeled cholesterol represented by the following formula (IV):

[Formula 4]

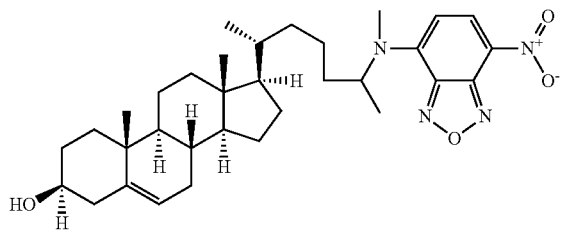

(IV)

(25-[N-[(7-nitro-2-1,3-benzoxadiazole-4-yl)methyl]amino]-27-norcholesterol, product name 25-NBD Cholesterol, CAS No: 105539-27-3, available from Avanti Polar Lipids, Inc.).

In the embodiment, the contact of a lipoprotein in a sample with labeled cholesterol can be performed by, for example, mixing the sample with a labeled cholesterol solution. After being mixed, the lipoprotein starts to absorb the labeled cholesterol. In the embodiment, there is no particular limitation as to the additive amount of labeled cholesterol. A slightly excessive amount of labeled cholesterol may be added in order to avoid the labeled cholesterol being depleted. For example, the labeled cholesterol may be added to the sample at a final concentration of 0.1 μM to 30 μM, preferably 1 μM to 10 μM. There is no particular limitation as to the temperature conditions and the contact time in the step. For example, the mixture of the sample and the labeled cholesterol may be incubated at 25° C. to 40° C., preferably 35° C. to 38° C. for 1 minutes to 24 hours, preferably 1 hour to 4 hours. The mixture may be allowed to stand or may be stirred or shaken during incubation.

In the embodiment, the step of removing labeled free cholesterol that is not incorporated into the lipoprotein may be further performed. For example, the labeled free cholesterol which is not incorporated into the lipoprotein can be removed by recovering only the lipoprotein by ultracentrifugation. In the embodiment, after removing the labeled free cholesterol, the recovered lipoprotein may be washed with a suitable aqueous medium such as PBS.

In the measurement method of the embodiment, the step to be performed is the step of bringing the lipoprotein having the labeled cholesterol into contact with an antibody that binds to a lipoprotein to form a complex of the lipoprotein and the antibody. In the embodiment, there is no particular limitation as to the antibody that binds to a lipoprotein so long as it is an antibody capable of specifically binding to a part of the surface of the lipoprotein. Preferably, the antibody is an antibody capable of specifically binding to an apolipoprotein as a main component of the lipoprotein. Examples of antibodies include anti-ApoAI antibodies and anti-ApoAII antibodies. Among them, anti-ApoAI antibodies are particularly preferred. In the embodiment, commercially available anti-lipoprotein antibodies and anti-ApoAI antibodies may be used.

The antibody that binds to a lipoprotein may be a monoclonal antibody or a polyclonal antibody. There is no particular limitation as to the origin of antibodies. The antibodies may be originated from mammals such as mice, rats, hamsters, rabbits, goats, horses, and camels. The isotype of the antibodies may be any of IgG, IgM, IgE, and IgA. It is preferable to use IgG. The antibodies include antibody fragments and derivatives thereof. Examples thereof include Fab fragments and F(ab')2 fragments.

When an anti-ApoAI antibody is used as the antibody that binds to a lipoprotein, the lipoprotein may be treated with an oxidant before bringing the antibody into contact with the lipoprotein having labeled cholesterol. The effect of the oxidant may result in an improvement in the reactivity of the anti-ApoAI antibody and the lipoprotein. Examples of oxidants include hydrogen peroxide, peroxynitrite, and chlorine dioxide.

In the embodiment, the contact of a lipoprotein having labeled cholesterol with an antibody that binds to a lipoprotein may be performed by, for example, mixing a solution containing the lipoprotein with a solution of the antibody. After being mixed, the lipoprotein binds to the antibody to form a complex. There is no particular limitation as to the additive amount of the antibody that binds to a lipoprotein, and it may be appropriately set by those skilled in the art depending on the type of the antibody. There is no particular limitation as to the temperature conditions and the contact time in the step. For example, the mixture of the lipoprotein and the antibody may be incubated at 20° C. to 40° C., preferably 22° C. to 28° C. for 1 minutes to 8 hours, preferably 1 hour to 2 hours. The mixture may be allowed to stand or may be stirred or shaken during incubation.

In the embodiment, after the step of forming a complex of the lipoprotein and the antibody, it is preferable to perform a step of separating labeled free cholesterol and the complex by removing the labeled free cholesterol which is not incorporated into the lipoprotein. For example, the labeled free cholesterol which is not incorporated into the lipoprotein is removed by recovering only the complex by ultracentrifugation so that it is possible to separate the lipoprotein and the labeled free cholesterol. Alternatively, a complex may be brought into contact with a solid phase for trapping the complex after the step of forming a complex. The labeled free cholesterol which is not incorporated into the lipoprotein is removed by recovering the solid phase in which the complex is trapped so that it is possible to separate the complex and the labeled free cholesterol. In the embodiment, after removing the labeled free cholesterol, the recovered complex may be washed with a suitable aqueous medium such as PBS.

The solid phase is preferably a solid phase capable of trapping an antibody that binds to a lipoprotein in a complex. There is no particular limitation as to the type of the solid phase. Examples of solid phases include a solid phase of a material that physically adsorbs an antibody and a solid phase on which a molecule that is specifically bound to an antibody is immobilized. The molecule that is specifically bound to an antibody includes protein A or G and an antibody that specifically recognizes the antibody (i.e., a secondary antibody). Substances lying between an antibody and a solid phase may be used in combination with each other to bind the antibody to the solid phase. Examples of combinations of the substances include a combination of biotin and avidin (or streptoavidin), a combination of glutathione and glutathione-S-transferase, and a combination of hapten and an antihapten antibody. For example, when the antibody that binds to a lipoprotein is modified with biotin in advance, the antibody can be trapped by a solid phase on which avidin or streptoavidin is immobilized.

The solid phase material is selected from an organic polymer compound, an inorganic compound, and a biopolymer. Examples of organic polymer compounds include latex, polystyrene, polypropylene, a styrene-methacrylic acid copolymer, a styrene-glycidyl(meth)acrylate copolymer, a styrene-styrene sulfonate copolymer, a methacrylic acid polymer, an acrylic acid polymer, an acrylonitrile-butadiene-styrene copolymer, a vinyl chloride-acrylic ester copolymer, and polyvinyl acetate acrylate. Examples of inorganic compounds include magnetic materials (e.g., iron oxide, chromic oxide, cobalt, and ferrite), silica, alumina, and glass. Examples of biopolymers include insoluble agarose, insoluble dextran, gelatin, and cellulose. These materials may be used in combination of two or more kinds thereof. There is no particular limitation as to the shape of the solid phase. Examples thereof include particles, microplates, microtubes, and test tubes.

In another embodiment, an antibody that binds to a lipoprotein, preferably an anti-ApoAI antibody is immobilized on a solid phase in advance, and the antibody immobilized on the solid phase is brought into contact with the lipoprotein having labeled cholesterol.

In the measurement method of the embodiment, the step of measuring the label generated from the complex is performed. Depending on the type of the label, any conventionally known method can be used. In the measurement step, the intensity of the label or changes in wavelength can be measured. Since the measurement result reflects the amount of the labeled cholesterol incorporated into the lipoprotein, it provides an indication of a lipoprotein's cholesterol uptake capacity. Therefore, the measurement method may also be referred to as "method of evaluating a lipoprotein's cholesterol uptake capacity based on the label generated from a complex of the lipoprotein having labeled cholesterol and the antibody that binds to a lipoprotein.

When fluorescence-labeled cholesterol is used, the fluorescence intensity can be measured. The method of measuring the fluorescence intensity is known in the art. For example, any known measurement device such as a spectrophotofluorometer or a fluorescence plate reader may be used to measure the fluorescence intensity generated from the complex. The excitation and fluorescence wavelengths can be appropriately determined depending on the type of the fluorescence-labeled cholesterol used. For example, when the fluorescence-labeled cholesterol of formula (III) or (IV) is used, the excitation wavelength may be determined from the range of 470 nm to 490 nm and the fluorescence wavelength may be determined from the range of 525 nm to 550 nm.

In the embodiment, a calibration curve may be created by preparing a dilution series of the labeled cholesterol having a known concentration and measuring the label. Based on the calibration curve, the labeled cholesterol incorporated into a lipoprotein in a sample can be quantified.

In the embodiment, the label may be measured after adding a surfactant such as a reagent with a degreasing action (e.g., cyclodextrin or CHAPS). When such a reagent is added, the labeled cholesterol incorporated leaks out of the lipoprotein. This results in more accurate measurement.

In another embodiment, the result of the lipoprotein's capacity to accept cholesterol which is obtained by the measurement method may be utilized to determine whether a subject has dyslipidemia. Hence, there is provided a method of supporting the determination of dyslipidemia, comprising the steps of:

bringing a lipoprotein in a sample obtained from a subject into contact with labeled cholesterol to incorporate the lipoprotein into the labeled cholesterol;

bringing the lipoprotein having the labeled cholesterol into contact with an antibody that binds to a lipoprotein to form a complex of the lipoprotein and the antibody;

measuring the label incorporated into the complex; and obtaining information on dyslipidemia of the subject based on the measurement result.

The accumulation of data of the measurement results of labels obtained from samples of healthy individuals and patients with dyslipidemia by the measurement method allows for the determination of a threshold or reference range based on the lipoprotein's capacity to accept cholesterol. The threshold or reference range is compared to the measurement result when using a sample of a subject so that it is possible to obtain information on dyslipidemia of the subject, i.e., information on whether the lipoprotein's capacity to accept cholesterol of the subject is normal or in the reference range. Based on the information, it is possible to support the determination of whether the subject has dyslipidemia.

In another embodiment, there is provided a reagent kit to be used for the measurement method. In other words, there is provided a reagent kit for measuring a lipoprotein's capacity to accept cholesterol, comprising: a first reagent containing labeled cholesterol; and a second reagent containing an antibody that binds to a lipoprotein (hereinafter, simply referred to as "reagent kit").

Figure 5A:
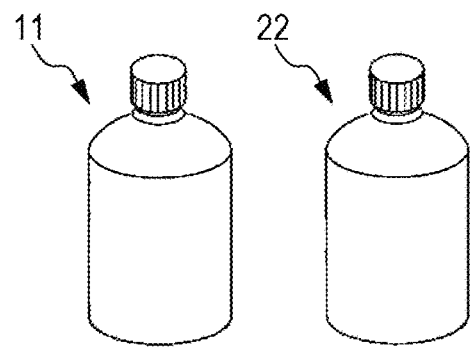
FIG. 5A is a view showing an example of a reagent kit of an embodiment, wherein 11 denotes a first reagent containing labeled cholesterol and 22 denotes a second reagent containing an antibody that binds to a lipoprotein.

The form of the first reagent containing labeled cholesterol may be a powder or a solution. The form of the second reagent containing an antibody that binds to a lipoprotein may be a solution or a freeze-dried product. In the embodiment, it is preferable that the first reagent and the second reagent are stored in a separate container or separately packed. The details of a sample, labeled cholesterol, an antibody that binds to a lipoprotein, and handling thereof are the same as those described in the measurement method. FIG. 5A shows an example of the reagent kit of the embodiment.

Figure 5B:
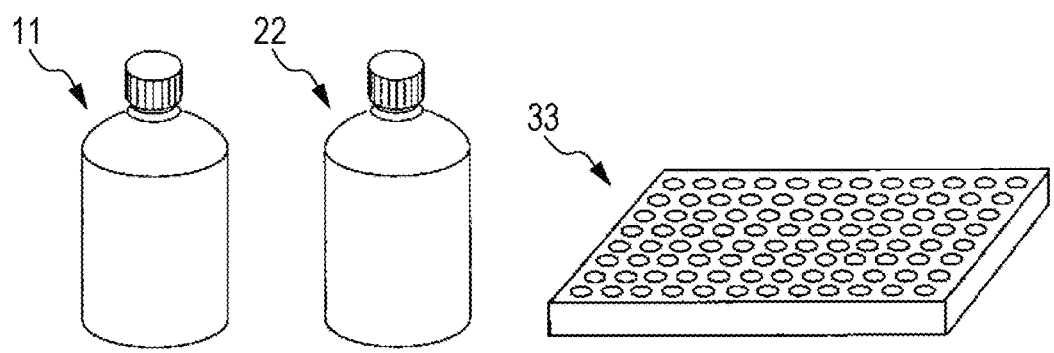
FIG. 5B is a view showing an example of a reagent kit of an embodiment which includes labeled cholesterol, an antibody that binds to a lipoprotein, and a solid phase, wherein 11 denotes a first reagent containing labeled cholesterol, 22 denotes a second reagent containing an antibody that binds to a lipoprotein, and 33 denotes a solid phase (96-well microplate)

The reagent kit may further include a solid phase to allow the antibody that binds to a lipoprotein to be immobilized thereon. In this case, it is preferable that the first reagent containing labeled cholesterol, the second reagent containing an antibody that binds to a lipoprotein, and the solid phase are stored in a separate container or separately packed. FIG. 5B shows an example of the reagent kit including the solid phase. The details of the solid phase are the same as the measurement method.

Figure 5C:
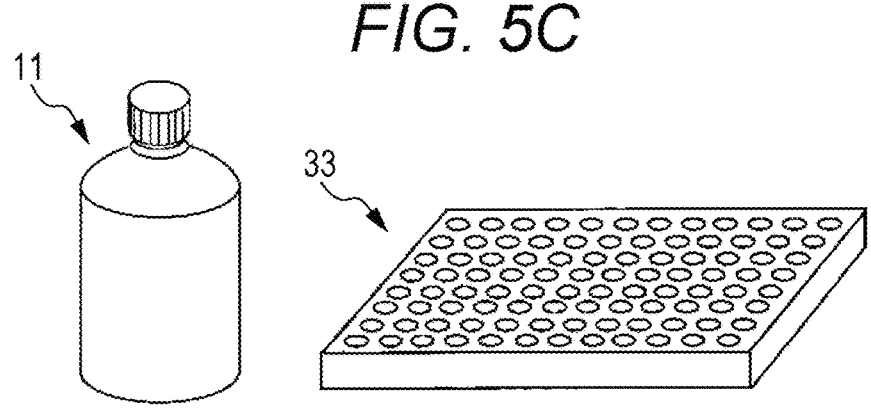
FIG. 5C is a view showing an example of a reagent kit of an embodiment which includes labeled cholesterol and a solid phase on which an antibody that binds to a lipoprotein is immobilized, wherein 11 denotes a first reagent containing labeled cholesterol and 33 denotes a solid phase on which an antibody that binds to a lipoprotein is immobilized (96-well microplate).

The antibody that binds to a lipoprotein, preferably an anti-ApoAI antibody may be immobilized on the solid phase in advance. In this case, the reagent kit is configured to include the first reagent containing labeled cholesterol and the solid phase on which the antibody that binds to a lipoprotein is immobilized. FIG. 5C shows an example of the reagent kit of the embodiment.

If necessary, the reagent kit may further include an aqueous medium for diluting a sample, a blocking agent, a fatty acid for esterifying cholesterol or a composition containing thereof, or an oxidant as a separate reagent. The details of these materials are the same as described in the measurement method.

Hereinafter, the present disclosure will be described in detail with reference to examples; however the present disclosure is not limited to the examples.

EXAMPLES

Example 1: Examination of Esterification of Boron-Dipyrromethene Labeled Cholesterol by HDL In the living body, HDL esterifies cholesterol and absorbs it. Accordingly, in this example, it was examined whether BODIPY labeled cholesterol was esterified depending on the LCAT activity of HDL.
(1-1) Extraction of HDL Fractions
To serum from healthy individuals (0.1 ml), an equivalent amount of 22% polyethylene glycol 4000 (Wako Pure Chemical Industries, Ltd.) was added. Then, the mixture was suspended. The obtained suspension was allowed to stand at room temperature for 20 minutes, followed by centrifugation at 3000 rpm at room temperature for 15 minutes. The supernatant was recovered as HDL fractions and stored at 4° C.
(1-2) Esterification of BODIPY Labeled Cholesterol
To the HDL fractions (20 µl) obtained in the above manner, 0.4 µl of 100 mM iodoacetamide (IAA) (Wako Pure Chemical Industries, Ltd.) (final concentration: 2 mM) as a LCAT inhibitor, 0.4 µL of 100 mM 5,5'-dithiobis-(2-nitrobenzoic acid) (DTNB) (DOJINDO LABORATORIES) (final concentration: 2 mM) or an equivalent amount of water was added. Then, the mixture was shaken at 800 rpm at 37° C. for 1 hour. A part of the obtained HDL-containing solution was taken out, and the ApoAI concentration was measured using ApoAI measurement kit (N-Assay TIA ApoAI-H, NITTOBO MEDICAL CO., LTD.). The specific procedure was performed in accordance with the manual attached to the kit. After measurement, the HDL-containing solution was diluted with a reaction buffer (PBS containing 2% BSA and 2 mM liposome (manufactured by Nippon Fine Chemical, Inc.) so as to have an ApoAI concentration of 100 µg/ml. The composition of the liposome contained in the reaction buffer includes 2 mM dimyristoyl phosphatidylglycerol (DMPG), 2 mM cholesterol, and 4 mM hydrogenated soybean phosphatidylcholine (HSPC). PBS was prepared by dissolving Phosphate buffered saline tablet (Sigma-Aldrich) in water. To the obtained diluent (50 µl), 0.5 µl of 0.5 mM BODIPY labeled cholesterol (TopFluor Cholesterol, Avanti Polar Lipids, Inc.) was added (final concentration: 5 µM). The mixture was shaken at 800 rpm at 37° C. overnight. Then, a Pasteur pipette was used to place the obtained solution onto a glass substrate coated with silica gel, followed by thin layer chromatography (TLC). As a developing solvent, a mixed solvent of tetrahydrofuran (THF), hexane, and acetic acid at a ratio of 3:7:0.2 was used. The fluorescence-labeled cholesterol developed on the substrate was detected at an excitation wavelength of 488 nm using the fluorescence imager (PharosFX, manufactured by Bio-Rad Laboratories, Inc.). The results are shown in FIG. 1.
(1-3) Results
As shown in FIG. 1, in the lane obtained by bringing HDL into contact with BODIPY labeled cholesterol (lane No. 2), a band showing the migration distance different from that of the BODIPY labeled cholesterol itself was detected. However, such a lane was not detected in the lanes (lane Nos. 3 and 4) to which the LCAT inhibitor was added. This band is considered to be a band of the BODIPY labeled cholesterol esterified by LCAT of HDL. Therefore, it is confirmed that the BODIPY labeled cholesterol is esterified depending on the LCAT activity of HDL from healthy individuals.

Figure 2:
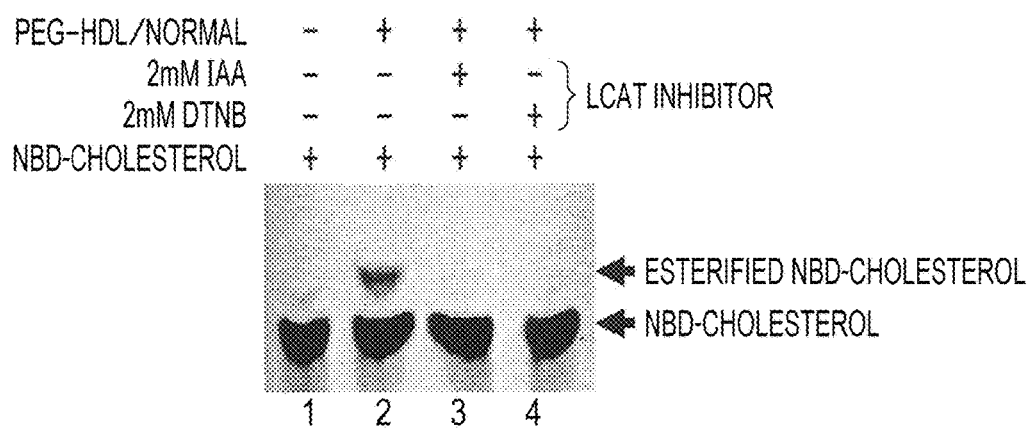
FIG. 2 is a photograph showing that fluorescence-labeled cholesterol including a fluorophore having a benzoxadiazole skeleton is esterified by HDL.

Example 2: Examination of Esterification of Nitrobenzoxadiazole (NBD) Labeled Cholesterol by HDL In this example, it was examined whether NBD labeled cholesterol was esterified depending on the LCAT activity of HDL.
(2-1) Esterification of NBD Labeled Cholesterol
To the HDL fractions (20 µl) obtained from the serum samples of healthy individuals, 0.4 µl of 100 mM IAA (final concentration: 2 mM) as a LCAT inhibitor, 0.4 µL of 100 mM DTNB (final concentration: 2 mM) or an equivalent amount of water was added in the same manner as Example 1. Then, the mixture was shaken at 800 rpm at 37° C. for 1 hour. A part of the obtained HDL-containing solution was taken out, and the ApoAI concentration was measured in the same manner as Example 1. After measurement, the HDL-containing solution was diluted with a reaction buffer so as to have an ApoAI concentration of 100 µg/ml. To the obtained diluent (50 µl), 1 µl of 1 mM NBD labeled cholesterol (25-NBD Cholesterol, Avanti Polar Lipids, Inc.) was added (final concentration: 20 µM). Then, the mixture was shaken at 800 rpm at 37° C. for 2 hours. Then, a Pasteur pipette was used to place the obtained solution onto a glass substrate coated with silica gel, followed by TLC. The same mixed solvent as that of Example 1 was used as the developing solvent. The fluorescence-labeled cholesterol developed on the substrate was detected at an excitation wavelength of 488 nm using the fluorescence imager (PharosFX, manufactured by Bio-Rad Laboratories, Inc.). The results are shown in FIG. 2.
(2-2) Results
As shown in FIG. 2, in the lane obtained by bringing HDL into contact with NBD labeled cholesterol (lane No. 2), a band showing the migration distance different from that of the NBD labeled cholesterol itself was detected. However, such a lane was not detected in the lanes (lane Nos. 3 and 4)

to which the LCAT inhibitor was added. This band is considered to be a band of the NBD labeled cholesterol esterified by LCAT of HDL. Therefore, it is confirmed that the NBD labeled cholesterol is esterified depending on the LCAT activity of HDL from healthy individuals.

Example 3: Comparison of Method of Embodiment, to Conventional Method

In this example, the result measured by the method of the embodiment using the BODIPY labeled cholesterol and the antibody for trapping HDL was compared to the result measured by the conventional method using cultured cells. Then, the performance of the method of the embodiment was evaluated.

(3-1) Extraction of HDL Fractions

HDL fractions were obtained from human-serum samples (n=12) using PEG4000 in the same manner as Example 1. These HDL fractions were used as samples for the following procedure.

(3-2) Measurement by Method of Embodiment (i) Preparation of Measuring Plate

To each of the wells of a 96-well microplate (Black plate H for measuring fluorescence, manufactured by Sumitomo Bakelite Co., Ltd.) as a solid phase, 200 μl of 50 mM Tris-HCl (pH 7.5) was added. This washing procedure was performed twice in total. To each of the wells, 100 μl of an anti-ApoAI antibody (MONO5030, SANBIO, Inc.) solution prepared by diluting with 50 mM Tris-HCl (pH 7.5) so as to have a concentration of 10 μg/ml was added. Each of the mixtures was allowed to stand at 4° C. overnight or more. The antibody solution was removed. To each of the well, 200 μl of PBS was added, followed by washing. This washing procedure was performed three times in total. To each of the wells, 200 μl of 4% BSA/PBS was added. Each of the mixtures was shaken at 500 rpm at 25° C. for 3 hours.

(ii) Preparation of Measurement Samples (Contact of HDL with Labeled Cholesterol)

A part of each of the obtained HDL fractions was taken out, and the ApoAI concentration was measured in the same manner as Example 1. After measurement, each of the HDL fractions was diluted by adding an equivalent amount of a reaction buffer so as to have an ApoAI concentration of 0.1 μg/ml or less. To each of the obtained diluents (300 μl), 3 μl of 0.5 mM BODIPY labeled cholesterol (TopFluor Cholesterol, Avanti Polar Lipids, Inc.) was added (final concentration: 5 μM). The resultant mixtures were shaken at 800 rpm at 37° C. for 2 hours. To each of the obtained solutions (303 μl), 34 μl of an oxidant (8.8 M hydrogen peroxide, 1.76 mM sodium nitrite, and 0.86 mM DTPA) was added (final concentrations: 1 M, 0.2 mM, and 0.1 mM). These solutions were shaken at 800 rpm at 37° C. for 1 hour. Then, measurement samples containing HDL into which labeled cholesterol was incorporated were obtained.

(iii) Formation of Complex of HDL and Anti-ApoAI Antibody and Measurement of Fluorescence Intensity The BSA solution was removed from the 96-well microplate. 100 μl of each of the measurement samples was added to each of the wells. The plate was shaken at 600 rpm at 25° C. for 1 hour to form a complex of the HDL and the anti-ApoAI antibody. Each of the measurement samples was removed from the plate. To each of the well, 200 μl of PBS was added, followed by washing. This washing procedure was performed five times in total. To each of the wells, 100 μl of 10 mM cyclodextrin/PBS was added, followed by shaking at 600 rpm at 25° C. for 15 minutes. The fluorescence intensity was measured with a fluorescence plate reader (Infinite® 200 Pro, manufactured by TECAN) (excitation light: 485 nm/fluorescence light: 535 nm).

(3-3) Measurement by Conventional Method (i) Preparation of Samples

DMEM culture medium containing 10% FBS (400 μl culture medium/well) was used to seed mouse macrophage-like cell lines J774A.1 in 48-well plates (manufactured by IWAKI) at a concentration of 70,000 cells/well. After culturing for one day, the culture medium was removed. To each of the wells, 200 μl of each of 10 mM methyl-β-cyclodextrin, 10% FBS, 0.9 μM BODIPY labeled cholesterol (TopFluor Cholesterol, Avanti Polar Lipids, Inc.), and DMEM culture medium containing phenol red was added. To other wells as controls, 200 μl of each of 10 mM methyl-β-cyclodextrin, 10% FBS, and DMEM culture medium containing DMSO (900-fold diluted) and phenol red was added. The cells were incubated in a 5% $CO_2$ atmosphere at 37° C. for 2.5 hours. The culture medium was removed by aspiration. Each of the wells was washed by adding 400 μl of DMEM culture medium without serum and phenol red. To each of the wells, 200 μl of the DMEM culture medium without serum and phenol red which contained the HDL fractions at an HDL concentration of 0.78 μg/ml was added. To other wells as other controls was added 200 μl of the DMEM culture medium which contained ApoAI recombinant protein at a concentration of 6 μg/ml but free of serum and phenol red. The plate was incubated in a 5% $CO_2$ atmosphere at 37° C. for 24 hours.

(ii) Measurement of Fluorescence Intensity

The culture supernatant of each of the wells was transferred to a new 96-well V-bottom plate, followed by centrifugation at 1600 rpm at room temperature for 2 minutes. The obtained supernatant (180 μl/well) was transferred to a new 96-well flat-bottom black plate (manufactured by Corning Incorporated or SUMILON). The fluorescence intensity of the serum was measured with a fluorescence plate reader (Infinite® 200 Pro, manufactured by TECAN) (excitation light: 485 nm/fluorescence light: 535 nm). To each of the wells of a 48-well plate from which the culture supernatant was removed, 500 μl of PBS was added for washing. To each of the wells, 500 μl of a solubilizing buffer (50 mM Tris-HCl (pH 7.5), 1% CHAPS, 5 mM EDTA (pH 8.0), and 150 mM NaCl) was added. The cells were dissolved by shaking the plate at 450 rpm at 25° C. for 15 minutes. The cell lysate (200 μl) recovered from each of the wells was added to the corresponding well of the 96-well flat-bottom black plate to which the supernatant had been transferred. The fluorescence intensity of the mixture of the supernatant and the cell lysate was measured with a fluorescence plate reader (Infinite® 200 Pro, manufactured by TECAN) (excitation light: 485 nm/fluorescence light: 535 nm).

(3-4) Comparison

Figure 3:
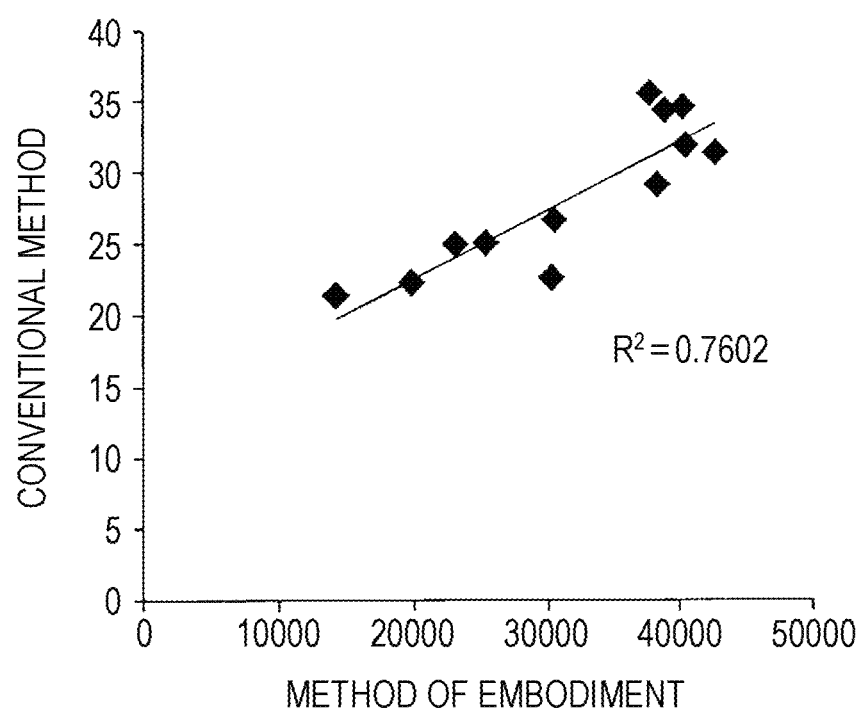
FIG. 3 is a scatter diagram showing that the results measured by a method of an embodiment are correlated with the results measured by a conventional method.

When data on each of the serum samples was plotted by plotting the measurement result by the method of the embodiment on a horizontal axis and plotting the measurement result by the conventional method on a vertical axis, a scatter diagram approximated to a straight line was created. This diagram is shown in FIG. 3. A determination coefficient $R^2$ calculated with Excel (Microsoft) was 0.7602. Therefore, the result obtained by measuring the HDL's capacity to accept cholesterol using the BODIPY labeled cholesterol and the antibody for trapping HDL is correlated with the measurement result obtained by the conventional method using cultured cells. It is confirmed that the method of the embodiment shows the same performance as that of the conventional method.

Comparative Example: Examination of Procedure of Preparing Measurement Samples

In this comparative example, the case of measurement according to the procedure of incorporating the fluorescence-labeled cholesterol after trapping of HDL by the antibody was examined.

(4-1) Extraction of HDL Fractions

HDL fractions were obtained from human-serum samples (samples 1 and 2) using PEG4000 in the same manner as Example 1.

(4-2) Preparation of Measuring Plate

Anti-ApoAI antibody (MON05030, SANBIO, Inc.) was solid-phased in each well of the 96-well microplate in the same manner as described in the method of the embodiment of Example 3, followed by blocking with a BSA solution. Thus, a measuring plate was prepared.

(4-3) Measurement of Fluorescence Intensity (i) Formation of Complex of HDL and Anti-ApoAI Antibody A part of each of the obtained HDL fractions was taken out, and the ApoAI concentration was measured in the same manner as Example 1. After measurement, each of the HDL fractions was diluted with a reaction buffer so as to have an ApoAI concentration of 0.1 µg/ml. To each of the obtained solutions (300 µl), 34 µl of an oxidant (1 M hydrogen peroxide, 200 µM sodium nitrite, and 100 µM DTPA) was added. The resultant mixtures were shaken at 800 rpm at 37° C. for 1 hour. The BSA solution was removed from the measuring plate. To each of the wells, 100 µl of the HDL fractions reacted with the oxidant was added. As negative controls, wells not containing the HDL fractions were prepared. The plate was shaken at 600 rpm at 25° C. for 1 hour to form a complex of the HDL and the anti-ApoAI antibody. The HDL fractions were removed from the plate. Each of the wells was washed three times with PBS in the same manner as Example 3.

(ii) Contact of HDL with Fluorescent-Labeled Cholesterol and Measurement of Fluorescence Intensity Three µl of 0.5 mM BODIPY labeled cholesterol (TopFluor Cholesterol, Avanti Polar Lipids, Inc.) was mixed with 300 µl of a reaction buffer. The obtained mixture (303 µl) was mixed with an oxidant (34 µl). To each of the wells of the plate, 100 µl of the obtained labeled cholesterol solution was added. The plate was shaken at 800 rpm at 37° C. for 1 hour. The labeled cholesterol solution was removed from the plate. Each of the wells was washed five times with PBS. To each of the wells, 100 of 10 mM cyclodextrin/PBS was added, followed by shaking at 600 rpm at 25° C. for 15 minutes. The fluorescence intensity was measured with a fluorescence plate reader (Infinite® 200 Pro, manufactured by TECAN) (excitation light: 485 nm/fluorescence light: 535 nm).

(iii) Detection of HDL by Sandwich ELISA

The cyclodextrin solution was removed from the plate after the measurement. Each of the wells was washed three times with PBS. Goat anti-ApoAI serum of the kit for measuring ApoAI concentration (N-Assay TIA ApoAI-H, NITTOBO MEDICAL CO., LTD.) was 1000-fold diluted with a blocking buffer (StartingBlock, Thermo Fisher Scientific Inc.). To each of the wells, 100 µl of the obtained diluent was added. The plate was shaken at 600 rpm at 25° C. for 1 hour, and then the diluent was removed. Each of the wells was washed three times with PBS. Rabbit anti-goat IgG polyclonal antibody labeled with HRP (P 0449, Dako) was 1000-fold diluted with a blocking buffer (StartingBlock, Thermo Fisher Scientific Inc.). To each of the wells, 100 µl of the obtained diluent was added. The plate was shaken at 600 rpm at 25° C. for 1 hour, and then the diluent was removed. Each of the wells was washed three times with PBS. To each of the wells, 100 µl of a chemiluminescent substrate solution (SuperSignal ELISA Pico, 37069, Thermo Fisher Scientific, Inc.) was added. The plate was shaken at 600 rpm at 25° C. for 2 minutes, and then the amount of luminescence was measured with a microplate reader (Infinite® F200 Pro, manufactured by TECAN).

(4-4) Measurement Results and Discussion

Figure 4A:
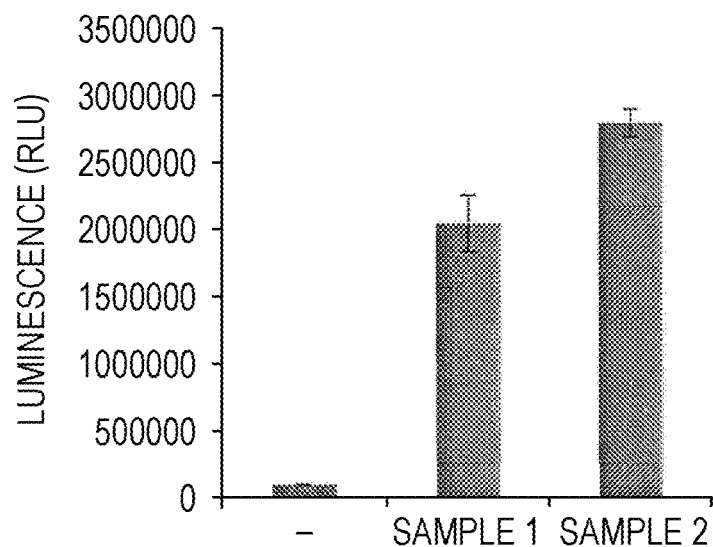
FIG. 4A is a graph showing that HDL is trapped by an anti-apolipoprotein AI (ApoAI) antibody immobilized on a solid phase by Sandwich ELISA.
Figure 4B:
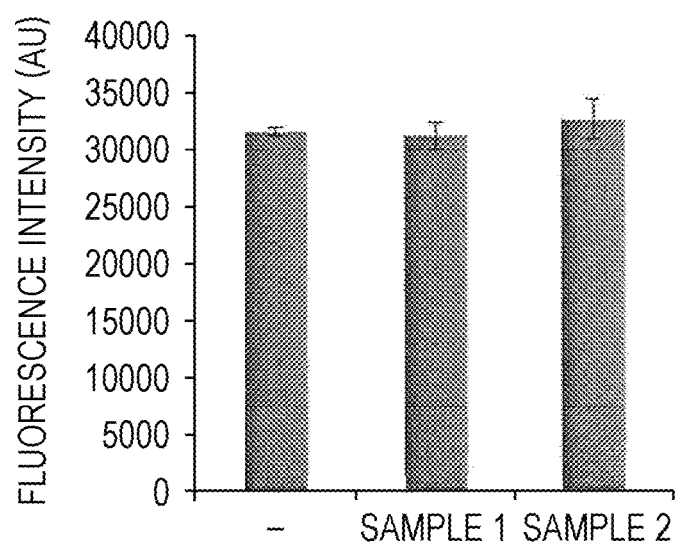
FIG. 4B is a graph showing that fluorescence-labeled cholesterol is not incorporated into the HDL trapped by the anti-ApoAI antibody.

The results of the detection of HDL by the ELISA method as well as the results of the fluorescence intensity are shown in FIGS. 4A and 4B. As shown in FIG. 4A, it is confirmed that the HDL in each serum sample is trapped by the anti-ApoAI antibody immobilized on the plate. As shown in FIG. 4B, regardless of the fact that the HDL fractions were brought into contact with the fluorescence-labeled cholesterol, the fluorescence intensity was the same as that of the negative control having no HDL. Consequently, it is found that even if HDL is brought into contact with labeled cholesterol after trapping the HDL by the anti-ApoAI antibody, the labeled cholesterol is not incorporated into the HDL.

The invention claimed is:

1. A method of measuring a lipoprotein's capacity to accept cholesterol comprising the steps of:
   bringing a lipoprotein in a sample into contact with labeled cholesterol to esterify the labeled cholesterol and incorporate the esterified labeled cholesterol into the lipoprotein;
   bringing the lipoprotein having the esterified labeled cholesterol into contact with an antibody that binds to the lipoprotein to form a complex of the lipoprotein and the antibody; and
   measuring the esterified labeled cholesterol incorporated into the lipoprotein of the complex.

2. The method according to claim 1, wherein the lipoprotein is a high-density lipoprotein.

3. The method according to claim 1, wherein the labeled cholesterol is fluorescence-labeled cholesterol, and the intensity of the fluorescence light from the complex is measured in the measurement step.

4. The method according to claim 1, wherein the step of incorporating the esterified labeled cholesterol into the lipoprotein, the step of forming the complex, and the step of measuring the esterified labeled cholesterol incorporated into the lipoprotein of the complex are performed in a cell-free system.

5. The method according to claim 1, further comprising a step of removing labeled free cholesterol which is not incorporated into the lipoprotein after the incorporation of the esterified labeled cholesterol into the lipoprotein.

6. The method according to claim 1, further comprising a step of separating labeled free cholesterol from the complex by removing the labeled free cholesterol which is not incorporated into the lipoprotein after the step of forming the complex.

7. The method according to claim 1, wherein the antibody that binds to the lipoprotein is an anti-ApoAI antibody.

8. The method according to claim 7, wherein the anti-ApoAI antibody is immobilized on a solid phase.

9. The method according to claim 1, wherein the sample is whole blood, serum or plasma.

10. The method according to claim 1, wherein the labeled cholesterol includes a fluorophore having a polar structure.

11. The method according to claim 1, wherein the labeled cholesterol comprises a fluorophore comprising a boron-dipyrromethene skeleton represented by the following formula (I):

[Formula 1]

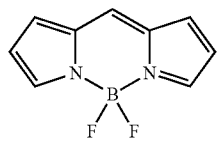

(I)

or a benzoxadiazole skeleton represented by the following formula (II):

[Formula 2]

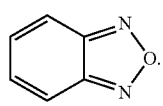

(II)

12. The method according to claim 11, wherein the fluorescence-labeled cholesterol comprising the fluorophore having the boron-dipyrromethene skeleton is fluorescence-labeled cholesterol represented by the following formula (III):

[Formula 3]

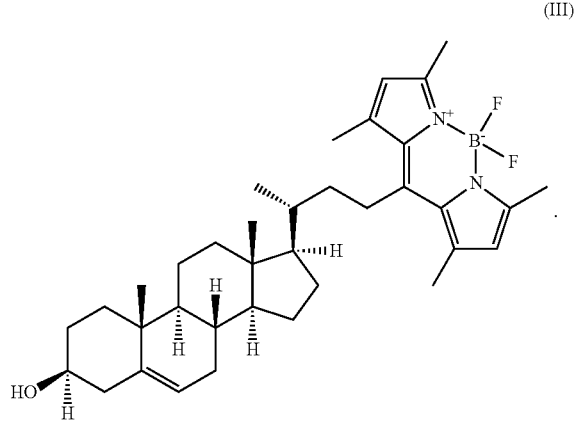

(III)

13. The method according to claim 11, wherein the fluorescence-labeled cholesterol comprising the fluorophore having the benzoxadiazole skeleton is fluorescence-labeled cholesterol represented by the following formula (IV):

[Formula 4]

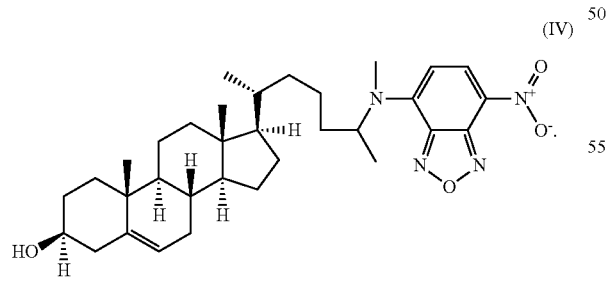

(IV)

14. A method of measuring a lipoprotein's capacity to accept cholesterol comprising the steps of:

bringing a high-density lipoprotein in a sample into contact with labeled cholesterol to esterify the labeled cholesterol and incorporate the esterified labeled cholesterol into the high-density lipoprotein;

bringing the high-density lipoprotein having the esterified labeled cholesterol into contact with an antibody that binds to the high-density lipoprotein to form a complex of the high-density lipoprotein and the antibody; and measuring the esterified labeled cholesterol incorporated into the high-density lipoprotein of the complex, wherein the step of incorporating the esterified labeled cholesterol into the high-density lipoprotein, the step of forming the complex, and the step of measuring the esterified labeled cholesterol incorporated into the high-density lipoprotein of the complex are performed in a cell-free system.

15. The method according to claim 14, wherein the labeled cholesterol is fluorescence-labeled cholesterol, and the intensity of the fluorescence light from the complex is measured in the measurement step.

16. The method according to claim 14, further comprising a step of removing labeled free cholesterol which is not incorporated into the high-density lipoprotein after the incorporation of the esterified labeled cholesterol into the high-density lipoprotein.

17. The method according to claim 14, further comprising a step of separating labeled free cholesterol from the complex by removing the labeled free cholesterol which is not incorporated into the high-density lipoprotein after the step of forming ft the complex.

18. A method of measuring a lipoprotein's capacity to accept cholesterol comprising the steps of:

bringing a high-density lipoprotein in a sample into contact with labeled cholesterol to esterify the labeled cholesterol and incorporate the esterified labeled cholesterol into the high-density lipoprotein;

bringing the high-density lipoprotein having the esterified labeled cholesterol into contact with an anti-ApoAI antibody which is immobilized on a solid phase to form a complex of the high-density lipoprotein and the anti-ApoAI antibody on the solid phase; and measuring the esterified labeled cholesterol incorporated into the high-density lipoprotein of the complex, wherein the step of incorporating the esterified labeled cholesterol into the high-density lipoprotein, the step of forming the complex, and the step of measuring the esterified labeled cholesterol incorporated into the high density lipoprotein of the complex are performed in a cell-free system.

* * * * *